US012564479B2

(12) United States Patent　　　　(10) Patent No.: US 12,564,479 B2
Bergeyron　　　　　　　　　　　　　(45) Date of Patent: Mar. 3, 2026

(54) METHOD FOR MANUFACTURING AN ORTHODONTIC APPLIANCE

(71) Applicant: Patrice Bergeyron, Geneva (CH)

(72) Inventor: Patrice Bergeyron, Geneva (CH)

( * ) Notice: Subject to any disclaimer, the term of this patent is extended or adjusted under 35 U.S.C. 154(b) by 527 days.

(21) Appl. No.: 18/012,491

(22) PCT Filed: Jun. 23, 2021

(86) PCT No.: PCT/EP2021/067259
　　§ 371 (c)(1),
　　(2) Date: Dec. 22, 2022

(87) PCT Pub. No.: WO2021/260076
　　PCT Pub. Date: Dec. 30, 2021

(65) Prior Publication Data
　　US 2023/0248475 A1　　Aug. 10, 2023

(30) Foreign Application Priority Data

Jun. 23, 2020　(FR) ...................................... 2006550

(51) Int. Cl.
　　*A61C 7/00*　　　　(2006.01)
　　*A61B 34/10*　　　　(2016.01)
　　*A61C 13/00*　　　　(2006.01)
(52) U.S. Cl.
　　CPC .............. *A61C 7/002* (2013.01); *A61B 34/10* (2016.02); *A61C 13/0004* (2013.01); *A61B 2034/104* (2016.02); *A61B 2034/105* (2016.02)
(58) Field of Classification Search
　　None
　　See application file for complete search history.

(56) References Cited

U.S. PATENT DOCUMENTS

2004/0197727 A1* 10/2004 Sachdeva .................. A61C 7/00
　　　　　　　　　　　　　　　　　　　433/24
2015/0265374 A1* 9/2015 Masoud ............... G06V 40/171
　　　　　　　　　　　　　　　　　　　382/128

FOREIGN PATENT DOCUMENTS

EP　　　　3566673 A1　11/2019
WO　　2019040927 A1　2/2019

OTHER PUBLICATIONS

International Search Report corresponding to International Application No. PCT/EP2021/067259 dated Aug. 19, 2021, 6 pages.

* cited by examiner

*Primary Examiner* — Dov Popovici
(74) *Attorney, Agent, or Firm* — Ronald M. Kachmarik; Cooper Legal Group LLC

(57)　　　　　　　ABSTRACT

Method for manufacturing at least one orthodontic appliance to be worn by a patient, for carrying out a complex orthodontic treatment from an initial point in time to a final point in time. The treatment includes at least a first basic orthodontic treatment designed to change the morphology of the patient's head and at least a second basic orthodontic treatment, which is subsequent to the first basic treatment and is designed to modify the configuration of the teeth. The method includes: a) determining a solution defining rules for the complex treatment; then b) setting the parameters for the first basic treatment, and subsequently setting the parameters for the at least second basic treatment, in such a way that once the parameterization is complete, the complex treatment always respects the rules; and c) designing, by a computer, and manufacturing at least one orthodontic apparatus for the complex treatment.

16 Claims, 3 Drawing Sheets a) Determination of a regulation, preferably by means of a computer, defining rules for the complex orthodontic treatment b) Parameterization, by means of a computer, of basic orthodontic treatments, in such a way that after said parameterization, the complex orthodontic treatment still complies with said rules c) Design, by means of a computer, and manufacture of at least one orthodontic appliance adapted to said complex orthodontic treatment

[Fig 1]

|  |
|---|
| a) Determination of a regulation, preferably by means of a computer, defining rules for the complex orthodontic treatment |

|  |
|---|
| b) Parameterization, by means of a computer, of basic orthodontic treatments, in such a way that after said parameterization, the complex orthodontic treatment still complies with said rules |

|  |
|---|
| c) Design, by means of a computer, and manufacture of at least one orthodontic appliance adapted to said complex orthodontic treatment |

[Fig 2]

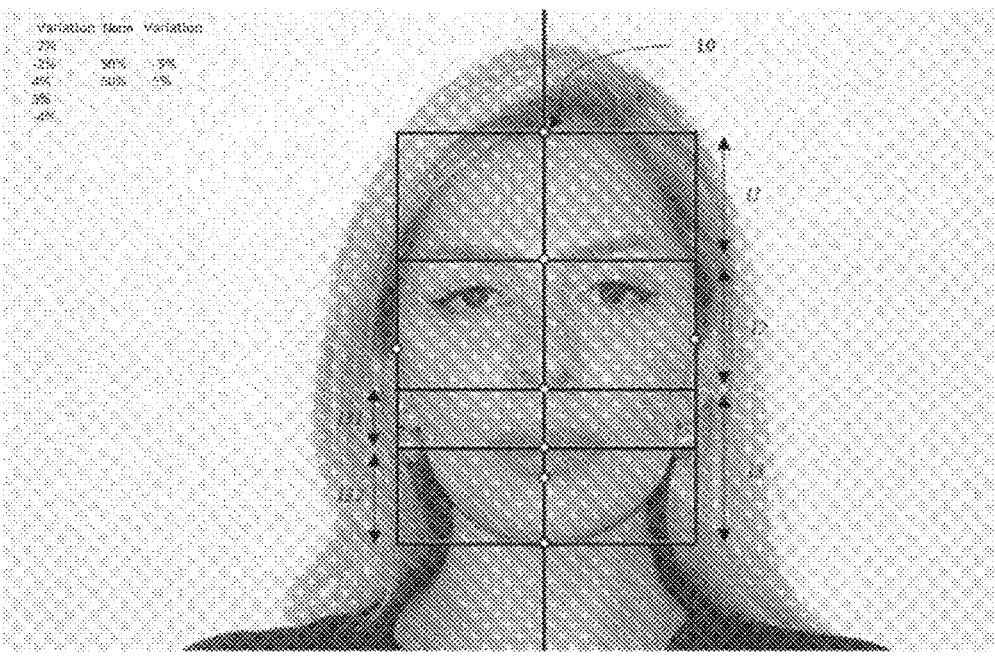

[Fig 3]
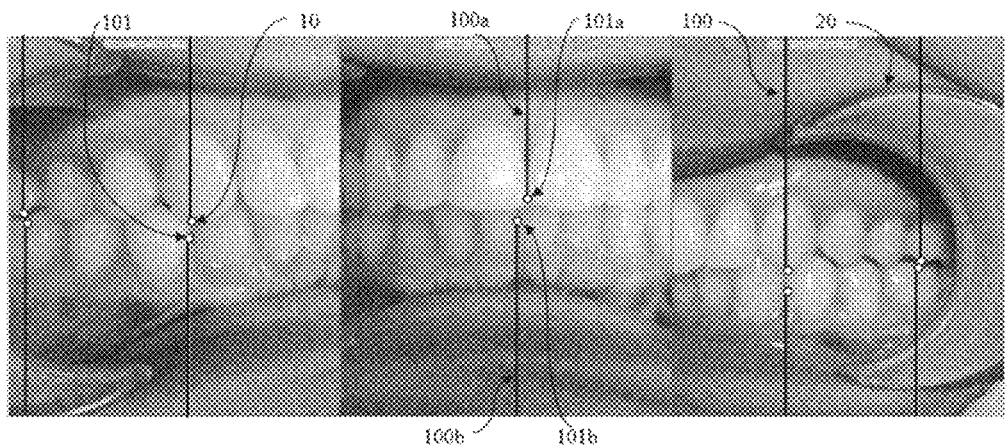
[Fig 4]
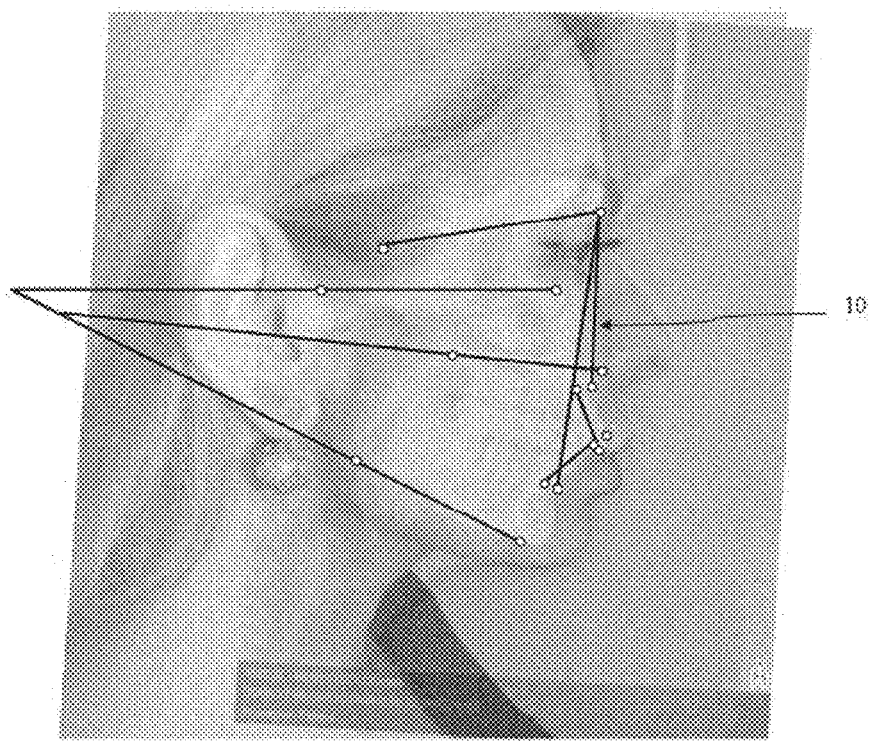

[Fig 5]
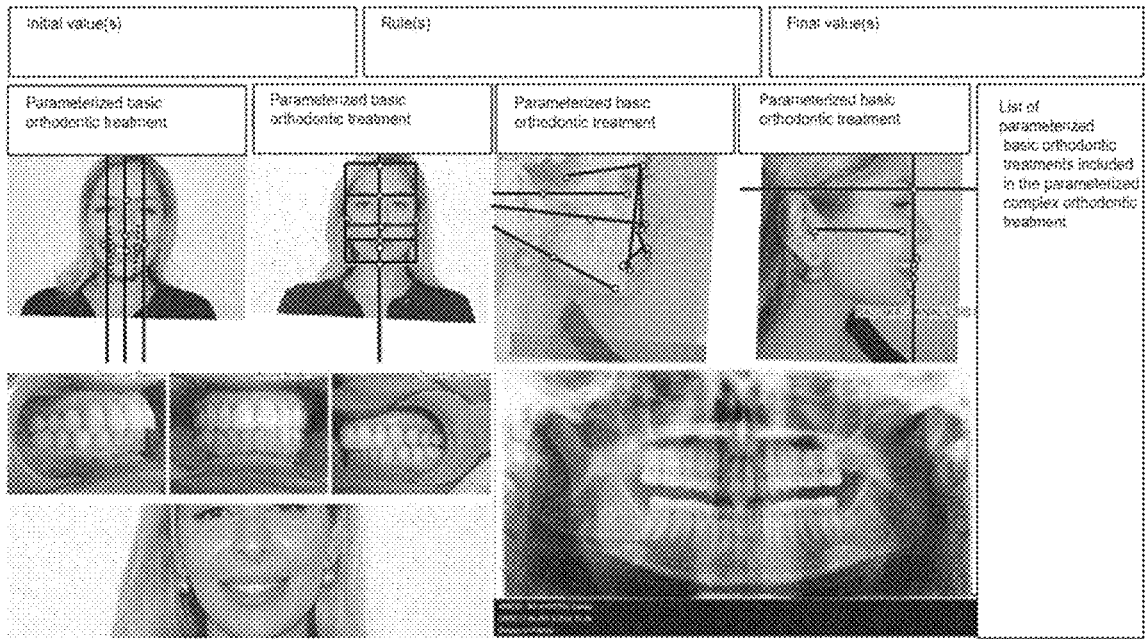

METHOD FOR MANUFACTURING AN ORTHODONTIC APPLIANCE

TECHNICAL FIELD

The present invention relates to a method for manufacturing an orthodontic appliance.

PRIOR ART

An orthodontic treatment uses an orthodontic appliance to move one or more of a patient's teeth. However, designing the orthodontic appliance is a very complex process and even when the orthodontist is experienced, it is still impossible for him/her to predict the exact effect of an orthodontic appliance. Thus, the patient is often not satisfied with the results obtained, the duration, the pain, or the cost of the orthodontic treatment or indeed the number of appointments with the orthodontist that the orthodontic treatment has involved.

There is therefore a need for a method for manufacturing an orthodontic appliance that yields results more in line with the wishes of the patient.

Furthermore, designing the orthodontic appliance takes a long time and there is a need for a method making it possible to manufacture an orthodontic appliance more quickly.

One aim of the invention is to meet these needs, at least partially.

DISCLOSURE OF THE INVENTION

Summary of the Invention

The invention proposes a method for manufacturing at least one orthodontic appliance intended to be worn by a patient, for the implementation, from an initial instant to a final instant, of a complex orthodontic treatment consisting of at least one first basic orthodontic treatment configured to change the morphology of the patient's head, preferably several said first basic orthodontic treatments, and at least one second basic orthodontic treatment configured to change the configuration of the patient's teeth, said method comprising the following steps:

a) determination, preferably by means of a computer, of a regulation defining rules for the complex orthodontic treatment; then b) parameterization, by means of a computer, of said at least one first basic orthodontic treatment, then of said at least one second basic orthodontic treatment, in such a way that the complex orthodontic treatment remains compliant with the regulation, that is to say that after said parameterization, it still complies with said rules;

c) design, by means of a computer, and manufacture of at least one orthodontic appliance adapted to said complex orthodontic treatment.

Preferably, any first basic orthodontic treatment is parameterized before any second basic orthodontic treatment. In other words, all of the first basic orthodontic treatments for changing the morphology of the patient's head are parameterized before the second basic orthodontic treatments for changing the configuration of the patient's teeth. Priority is therefore given to the morphology of the head, and the second basic orthodontic treatments cannot therefore, advantageously, result in an unacceptable morphology of the head.

As will be seen in more detail in the rest of the description, the manufacture of an orthodontic appliance according to the invention is no longer guided only by the objective of changing the configuration of the teeth, for example for the sole purpose of rectifying a malocclusion. It must also, indeed as a priority, comply with rules relating to the morphology of the head. The risk of the complex orthodontic treatment deforming the morphology of the head inappropriately, and therefore of the patient not being satisfied with the results obtained, is therefore reduced or even eliminated. In addition, the first basic orthodontic treatment may advantageously change the morphology of the patient's head in a way that meets the needs of the patient, in other words, give additional satisfaction to the patient.

The invention proposes a structured, computer-assisted approach, systematically taking into account the effect of various basic orthodontic treatments to ensure that their parameterization does not jeopardize compliance of the complex orthodontic treatment with the regulation. This approach results in an orthodontic treatment and an orthodontic appliance that are better suited to the patient's needs. The number of appointments with the orthodontist is advantageously thereby limited.

The method according to the invention may comprise one or more of the following optional features:

the final instant follows the initial instant by more than 2 weeks, 1 month, three months and/or less than 5 years, less than 3 years, or less than one year;

the complex orthodontic treatment preferably comprises more than 2, more than 5, more than 10, and/or less than 100 basic orthodontic treatments, preferably chosen from the group consisting of a treatment for moving the lower jaw up or down;

a treatment for changing the width of the upper jaw;

a treatment for changing the width of the lower jaw;

treatment for moving the lower jaw forward or backward;

a treatment for moving the upper jaw forward or backward;

a treatment for moving the lower jaw laterally;

a treatment for changing the transverse tilt of the jaws;

a treatment for moving one or more teeth;

a treatment for moving the gums;

a treatment for changing the color of one or more teeth, preferably a teeth whitening treatment.

the number and/or nature of the basic orthodontic treatments which constitute the complex orthodontic treatment may be modified by a user, preferably by the orthodontist;

to constitute the non-parameterized complex orthodontic treatment, that is to say before step b) of parameterization, the user chooses basic orthodontic treatments from a database of non-parameterized basic orthodontic treatment models, and places them in order;

the database comprises one or more models for one or more basic orthodontic treatments chosen from said group;

the basic orthodontic treatments are placed in order so as to be parameterized in the following order of parameterization:

parameterization of a treatment for moving the lower jaw, preferably comprising a parameterization of a treatment for moving the lower jaw vertically;

parametrization of a treatment for changing the width of the upper jaw;

parameterization of a treatment for changing the width of the lower jaw;

parametrization of a treatment for moving the lower jaw forward/backward;

parametrization of a treatment for moving the upper jaw forward/backward;

parametrization of a treatment for moving the lower jaw to the right/left;

parametrization of a treatment for tilting the jaws;

parametrization of a treatment for moving the gums;

parametrization of a treatment for moving one or more teeth;

wherein one or more of these basic orthodontic treatments may be absent.

the order of parametrization is defined, and preferably modifiable by a user, preferably by the patient and/or the orthodontist, preferably by the orthodontist;

the regulation defines:

at least one capital rule, that is to say a rule relating to the morphology of the head, preferably concerning a value chosen from the group consisting of a height of the face at the final instant, a height of the lower jaw and/or a height of the upper jaw at the final instant a width of the lower jaw at the final instant, a position of the lower jaw in relation to the upper jaw, at the final instant, a width of the upper jaw at the final instant, a position of the lower lip and/or the upper lip in relation to the chin and to the forehead;

at least one dental rule, that is to say a rule relating to the configuration of the teeth, preferably concerning a value chosen from the group consisting of a distance with respect to a target configuration of the teeth at the final instant;

a tilt with respect to a target configuration of the teeth at the final instant;

a movement of the gums with respect to a target configuration of the teeth at the final instant;

a target color of the teeth at the final instant;

at least one transverse rule, that is to say a rule which is neither a capital rule nor a dental rule, preferably concerning a value chosen from the group consisting of a cost for the complex orthodontic treatment, a duration for the complex orthodontic treatment, a pain coefficient for the complex orthodontic treatment, a comfort coefficient for the complex orthodontic treatment, one or more technical characteristics for said at least one orthodontic appliance;

the regulation, preferably at least some of the transverse rules, is determined, partially or completely, as a function of the patient, preferably as a function of choices made by the patient;

the regulation, preferably at least some of the transverse rules, is determined, partially or completely, on the basis of images, preferably photos, preferably in color and preferably in realistic color and/or on the basis of 3D models, preferably a 3D model of the face, and/or a 3D model of the inside of the mouth, referred to as "intraoral", in particular a 3D model of the teeth and/or a tomographic image or "cone beam" (CBCT) scan;

said images preferably comprise at least an image from the front and a profile image of the head, and in particular of the face, of the patient, and/or an image showing the patient's mouth in the open position and at least one image showing the patient's mouth in the closed position, and/or an image showing the patient's mouth in the smiling position, or "smiling image", preferably two images showing the patient's mouth in the smiling position comprising an image from the front and a profile, and/or a panoramic image of the dental arches, and/or an x-ray of the head, preferably at least one profile x-ray of the head, of the patient;

said 3D models preferably comprise at least one facial scan, that is to say a 3D model of the patient's face;

a rule defines, for a dimension of the head or teeth, a range of acceptable values for said dimension of the head or teeth at the final instant;

preferably at least some of the capital and/or dental rules each define a range of acceptable values, the limits of which are defined by means of a frame of reference, for a dimension of the head or of the teeth at the final instant;

said dimensions are determined on the basis of said images and/or said 3D models, preferably by a distance between noteworthy points of said images and/or said 3D models;

the user, preferably the orthodontist, identifies said noteworthy points in the images and/or 3D models displayed on the screen of the computer, arranges measurement marks as a function of the noteworthy points, and the computer determines said dimensions as a function of the arrangement of said measurement marks;

alternatively, the images and/or the 3D models are analyzed by computer, preferably by means of a machine learning method, preferably by means of a neural network, to determine said measurement marks and/or said noteworthy points and/or said dimensions;

noteworthy points are preferably chosen from the group consisting of the center of an eye of the patient, a point between the eyebrow arches, preferably located halfway between the eyebrows, a subnasal point, in particular located in the center under the nose, a point on the forehead, in particular located on the hairline, in particular in the middle of the forehead, and/or the most prominent point on the forehead in a profile view, the point at the end furthest to the right of the patient's face seen from the front, the point at the end furthest to the left of the patient's face seen from the front, a point located on the end of the chin, preferably in the middle of the chin, and/or the most prominent point on the chin in a profile view, a point located at a corner of the patient's lips, a point located on the contour of the lips, in particular on the end of the upper lip and/or the end of the lower lip, preferably the most prominent point, a point located at the junction of the lips when they are closed, in particular, the center of the mouth when the lips are closed, a point located at the junction between two teeth, in particular between the central incisors, a point located on the contour of a tooth, in particular a point located in the middle of the lower contour of an upper tooth and/or a point located in the middle of the upper contour of a lower tooth, for example a cusp point of a tooth or a depression between two cusps,

a point of contact between two teeth, in particular between an upper tooth and a lower tooth, a junction point between the enamel and the gum of a tooth, the tragion, the orbitale;

noteworthy points define or are used to define said frame of reference;

the user, preferably the orthodontist, identifies said noteworthy points in the images and/or the 3D models displayed on the screen of the computer, arranges reference marks as a function of the noteworthy points, and the computer determines the frame of reference as a function of the arrangement of said reference marks;

the reference marks are preferably chosen from the group consisting of a point, a straight line, a segment, and a circle;

alternatively, the images and/or the 3D models are analyzed by computer, preferably by means of a machine learning method, preferably by means of a neural network, to determine the frame of reference;

the regulation may be modified at an instant during the parameterization, preferably at any instant during the parameterization (step b)), as long as the complex orthodontic treatment, as parameterized up to this instant, complies with the regulation;

preferably, to parameterize a basic orthodontic treatment, a parameterization block is chosen, preferably by the orthodontist, from a group of potential parameterization blocks potentially applicable to the basic orthodontic treatment so as to parameterize same, preferably by selecting one of said potential parametrization blocks from a list displayed on the screen of the computer, the computer then parameterizing the basic orthodontic treatment with said parameterization block;

said group of potential parameterization blocks displayed to the user, preferably the orthodontist, comprises only parameterization blocks compatible with the regulation, that is to say parameterization blocks which, when applied to the basic orthodontic treatment, result in a complex orthodontic treatment that complies with the regulation;

at an instant during the parameterization, preferably at any instant during the parameterization, information is displayed, preferably on the screen of the computer, and is preferably updated in real time, this information relating to the regulation, for example the maximum cost for the complex orthodontic treatment, and/or parameters of the complex orthodontic treatment, for example the cost of the complex orthodontic treatment as parameterized at said instant, and/or the final morphology, that is to say the morphology at the final instant, resulting from the complex orthodontic treatment as parameterized at said instant (that is to say the morphology anticipated at the final instant if the complex orthodontic treatment was implemented), and/or the final configuration of the teeth, that is to say the configuration of the teeth at the final instant, resulting from the complex orthodontic treatment as parameterized at said instant;

said information comprises a representation, preferably realistic, of the teeth and/or of the head of the patient in the final configuration of the teeth and/or the final morphology, respectively;

to check, at an instant in step b), whether the complex orthodontic treatment complies with the regulation, dimensions in images and/or 3D models displayed on a computer screen are measured, preferably in step a), between noteworthy points in said images and/or in said 3D models, said dimensions constituting initial values of parameters of the complex orthodontic treatment, the effect of the complex orthodontic treatment, as parameterized at said instant in step b), is simulated on said dimensions, between the initial instant and the final instant, that is to say by anticipating the effect of the complex orthodontic treatment on these dimensions between the initial instant and the final instant, so as to determine final values for said parameters, then it is checked whether said final values fall within corresponding ranges defined by the rules of the regulation;

to determine said initial values, noteworthy points are identified in the images and/or the 3D models, and measurement marks are arranged as a function of the noteworthy points, said computer determining said initial values as a function of the arrangement of said measurement marks, or the images and/or the 3D models are analyzed by computer using a machine learning method to determine said initial values;

to define at least one limit of a said range relating to a position of a noteworthy point of the patient, at least one reference mark is arranged in at least one of said images and/or one of said 3D models, the position of the reference mark indicating an extreme position for said noteworthy point at the final instant, and thus defining said limit;

said at least one orthodontic appliance is an orthodontic aligner;

after step c), a report is generated comprising information relating to the regulation, and/or complex orthodontic treatment parameters, and/or a morphology resulting from the complex orthodontic treatment at the final instant, and/or a final configuration of the teeth resulting from the complex orthodontic treatment at the final instant;

said report is displayed to the orthodontist and/or to the patient, for example by being sent or by being displayed, for example on a screen;

said parameterization is displayed to a user to train said user in orthodontics.

The invention also relates to a computer program comprising code instructions for the execution, at least partially, of one or more steps a), b), and c), preferably of all of these steps when said program is executed by a computer, a computer medium on which such a program is recorded, for example a memory or CD-ROM, and a computer on which such a program is loaded.

The invention also relates to a kit comprising:

a device for acquiring images and/or 3D models, comprising for example a camera and/or a scanner, preferably a 3D scanner and/or a "cone beam" scanner;

a computer loaded with a computer program according to the invention.

Definitions

A "patient" is a person for whom a method according to the invention is implemented, regardless of whether or not this person is ill.

"Orthodontist" means any person qualified to provide orthodontic care, which also includes a dentist.

The user is the person who implements the method, conventionally the orthodontist, preferably with the patient.

A "retractor", or "dental retractor", is a device for pushing back the lips. It has an upper edge and a lower edge extending around a spacer opening. In the position of use, the upper and lower lips of the patient bear on the upper and lower edges, respectively. The retractor is configured to elastically separate the upper and lower lips from one another so as to expose the teeth visible through the opening. A retractor thus makes it possible to observe the teeth without the lips getting in the way.

"Image" means a two-dimensional image such as a photograph or an image taken from a film. An image is made up of pixels. A "photo" is an image that depicts an actual object as seen by the human eye, preferably in realistic colors. A tomographic image or a panoramic image acquired by X-ray are images that are not photos. An image may also be a view of a 3D model. A 3D model is a digital three-dimensional model. It is made up of a set of voxels. "Acquisition device" means any device for taking an image, which includes a camera, a mobile phone, a tablet or a computer.

"Capital image" means an image showing at least part of the patient's head.

"Dental image" means an image showing at least some of the patient's teeth.

A "rule" defines a constraint for the complex orthodontic treatment, for example "the cost must be less than €10,000", "the lower jaw must be moved forward by a distance between 1 and 5 mm", "tooth No. 17 must be rotated, about its axis, by 15°". The rules thus define the ranges of values that a complex orthodontic treatment parameter may take.

A "target" teeth configuration or head morphology is a teeth arrangement or head shape that it is desired to achieve at the final instant. The regulation may define that the target teeth configuration or head morphology must be reached at the final instant, possibly with a margin of tolerance.

A "basic orthodontic treatment" is an orthodontic treatment intended to act, through the use of an orthodontic appliance, on the morphology of the head and/or the configuration of the teeth. It is defined by this action, or "function". It becomes operational after parameterization, that is to say after application of a parameterization block.

Conventionally, a basic orthodontic treatment is intended to bring at least one value of a parameter closer to a corresponding target value, preferably in such a way that said value reaches the target value at the end of the basic orthodontic treatment.

In particular, a distinction is made between "capital" basic orthodontic treatments, which essentially act on the morphology of the head, and "dental" basic orthodontic treatments, which essentially act on the configuration of the teeth. A dental basic orthodontic treatment may act on the morphology of the head and, conversely, a capital basic orthodontic treatment may act on the configuration of the teeth. However, any basic orthodontic treatment has a principal action, on the morphology of the head or on the configuration of the teeth, which makes it possible to classify said treatment as a capital or dental basic orthodontic treatment.

Capital basic orthodontic treatments include in particular
a treatment for changing the position of the lower jaw in relation to the upper jaw,
a treatment for moving the lower jaw up or down;
a treatment for changing the width of the upper jaw;
a treatment for changing the width of the lower jaw;

a treatment for moving the lower jaw forward or backward;
a treatment for moving the upper jaw forward or backward;
a treatment for moving the lower jaw laterally;
a treatment for changing the width of the upper jaw,
a treatment for changing the width of the lower jaw,
a treatment for tilting the jaws.

A capital basic orthodontic treatment does not necessarily involve a change in the morphology of the patient's head. For example, if the regulation imposes a position of the lower jaw which is the position at the initial instant, that is to say it defines a range of values for the parameter "position of the lower jaw" which is limited to the initial value for this parameter, the capital basic orthodontic treatment must be parameterized to ensure that the position of the lower jaw will not be changed by the complex orthodontic treatment. Preferably, at least the first basic orthodontic treatment, which is capital, involves a change in the morphology of the patient's head.

Dental basic orthodontic treatments include in particular
a treatment for changing the configuration of the teeth, in particular a treatment for moving and/or tilting at least one tooth,
a treatment for moving the gums,
a treatment for changing the color of the teeth.

A distinction is made between the basic orthodontic treatments, which are well known, and the complex orthodontic treatment, which is a combination of basic orthodontic treatments.

A complex orthodontic treatment may comprise one or more first basic orthodontic treatments and one or more second basic orthodontic treatments.

To perform a basic orthodontic treatment, one or more solutions are possible. Each of these solutions is considered as the result of a particular parameterization of the basic orthodontic treatment. A parameterization block includes all of the information that makes it possible to parameterize the basic orthodontic treatment to constitute a particular solution, that is to say a particular embodiment, or "version", of the basic orthodontic treatment. Parameterization consists in setting a value or a range of acceptable values for at least one parameter of a basic orthodontic treatment, that is to say in establishing rules specific to a basic orthodontic treatment, unlike the rules of the regulation, which relate to the complex orthodontic treatment. In one embodiment, the parameterization of a basic orthodontic treatment consists in selecting a parameterization block from a group of parameterization blocks referred to as "potential" parameterization blocks. The selected parameterization block is said to be "active".

The rules of the regulation relate to the complex orthodontic treatment, but several basic orthodontic treatments may contribute to modifying the value of a parameter associated with a rule. For example, a rule may impose a movement of the lower jaw forward by 3 mm and several basic orthodontic treatments may have an effect on the position of the lower jaw. The order of parameterization results in the parameterization of a basic orthodontic treatment reducing the possibilities for parameterization of the basic orthodontic treatments parameterized subsequently.

At an instant during the parameterization step where one or more basic orthodontic treatments have been parameterized, the "parameterized" complex orthodontic treatment is that which includes this or these parameterized basic orthodontic treatments. The parameterization of the complex orthodontic treatment is therefore completed as the basic orthodontic treatments are parameterized.

For the sake of clarity, "capital" is used to refer to images showing at least part of the patient's head, to parameters relating to the morphology of the head, to values of these parameters, to rules for these parameters, to basic orthodontic treatments adapted to modify these values and to parameterization blocks for these basic orthodontic treatments.

For the sake of clarity, "dental" is used to refer to images showing at least some of the patient's teeth, to parameters relating to the position and/or orientation of the teeth, to values of these parameters, to rules for these parameters, to basic orthodontic treatments adapted to modify these values and to parameterization blocks for these basic orthodontic treatments.

A "range of values" is defined by lower and upper limits. It may contain only one value, the lower limit then being equal to the upper limit.

A "group" may comprise one or more elements.

"Computer" means any electronic device, which includes a set of several machines, having computer processing capabilities. Conventionally, a computer comprises in particular a processor, a memory, a man-machine interface, conventionally comprising a screen, a module for communication via the internet, WIFI, Bluetooth® or the telephone network. Software configured to implement the method of the invention is loaded onto the memory of the computer. The computer may also be connected to a printer.

The computer may be a server remote from the user, for example the "cloud".

"Active" (or "activated") designates a parameterization block applied to a basic orthodontic treatment. By extension, the basic orthodontic treatment may also be designated as active.

"Comprising" or "including" or "having" shall be construed as non-limiting, unless otherwise specified.

BRIEF DESCRIPTION OF THE DRAWINGS

Other features and advantages will become apparent on reading the detailed description which follows and on examining the appended drawing in which:

FIG. 1 schematically shows various steps of an embodiment of a method for manufacturing an orthodontic appliance according to the invention;

FIG. 2 shows an example of an image including measurement marks, in particular for the determination of capital rules and the parameterization of capital basic orthodontic treatments;

FIG. 3 shows an example of determination of images including measurement marks, in particular for the determination of dental rules and the parameterization of dental basic orthodontic treatments;

FIG. 4 shows an example of combining a profile photo and an X-ray; and

FIG. 5 shows a report relating to a complex orthodontic treatment parameterized according to the invention.

DETAILED DESCRIPTION

The following detailed description describes preferred embodiments, but is not limiting.

A method for manufacturing an orthodontic appliance includes the steps shown in FIG. 1. It is a computer-assisted method, preferably implemented by a computer, with the exception of the acquisition of the images and the manufacture of the orthodontic device.

It is based on the structured parameterization of a complex orthodontic treatment implementing one or more orthodontic appliances, between initial and final instants. In particular, the complex orthodontic treatment is designed to primarily comply with capital rules relating to the shape, or "morphology", of the patient's head. To parameterize the complex orthodontic treatment, the dental rules are taken into account only after at least some of the capital rules have been taken into account.

In step a), the rules are defined, that is to say a set of rules with which the complex orthodontic treatment must comply, whatever the level of parameterization thereof, that is to say the number of basic orthodontic treatments parameterized in step b).

The regulation may be universal, or may be defined for a group of individuals, for example for a set of individuals of the same age group or the same sex or sharing the same pathology. It is preferably specific to the patient.

The regulation may be defined by the patient and/or the orthodontist.

In one embodiment, the frame of reference initially consists at least partially of standard rules, and the definition of the regulation consists in specifying these standard rules to make them operational. For example, a standard rule might be "the maximum cost for the complex orthodontic treatment is X" and this is made operational after the user has entered the value of X, to become for example the following rule: "the maximum cost for the complex orthodontic treatment is €10,000".

As another example, a standard rule is "the distance between the pogonion point and the straight line connecting the most prominent point on the lower lip to the most prominent point on the forehead, in an image showing a side view of the head, must be less than Y" and this is made operational after the user has entered the value of Y, to become the following rule: "the distance between the pogonion point and the straight line connecting the most prominent point on the lower lip to the most prominent point on the forehead, in an image showing a side view of the head, must be less than 5 mm".

Rules may be predefined. For example, a rule may impose, by default, "the distance between the pogonion point and the straight line connecting the most prominent point on the lower lip to the most prominent point on the forehead, in an image showing a side view of the head, must be less than 10 mm". Preferably, the predefined rules may be modified.

A distinction may be made, in the regulation, between the "capital", "dental" and "transverse" rules.

Transverse Rules

A "transverse rule" is a rule that is neither a capital rule nor a dental rule. The transverse rules are preferably determined by the patient.

Preferably, the transverse rules specify a maximum cost and/or a maximum duration and/or a maximum value for a pain coefficient and/or a minimum value for a comfort coefficient preferably taking into account the number of appointments to be scheduled with the orthodontist, and/or a general technical characteristic for the orthodontic appliance to be manufactured, for example specifying that this orthodontic appliance must be an orthodontic aligner.

The transverse rules are preferably entered into the computer, for example using a keyboard.

Capital Rules

The "capital rules" are rules which impose ranges, defined by the frame of reference, for the values of the capital parameters, that is to say parameters relating to the shape of the head, at the final instant.

In one embodiment, the frame of reference defines a morphology of the head desired by the patient and/or the orthodontist, preferably by the patient, that is to say a target morphology. The target morphology may set a value for at least some of the capital parameters, or for each capital parameter, or authorize a range of several values for at least some of the capital parameters, or for each capital parameter.

In one embodiment, the target morphology is the morphology of the head at the initial instant, that is to say the regulation requires that the complex orthodontic treatment not change the dimensions of the patient's head. Preferably, however, the target morphology is different from the morphology of the head at the initial instant, that is to say the regulation requires that the complex orthodontic treatment change the dimensions of the patient's head.

A capital parameter may in particular be a dimension or an angle.

A capital parameter may in particular be chosen from:
- a distance between two points, for example a point located in the middle of the forehead on the hairline, and a point between the eyebrow arches, or between a point between the eyebrow arches and a subnasal point or between a subnasal point and a pogonion point;
- a distance between the two corners of the patient's lips when (s)he is smiling;
- a width for a dentition shown in a smiling image;
- a distance between a straight line passing through a point between the eyebrow arches and a subnasal point, and the inter-incisal point of the upper central incisors;
- a distance between a straight line passing through the junction of the first upper incisors and a straight line passing through the junction of the first lower incisors;
- an angle between a straight line passing through at least two points among a point between the eyebrow arches, a subnasal point and an inter-incisal point and a straight line passing through a point on the cusp of the first left or right premolar, and a point at the enamel-cementum junction of the first left or right premolar, respectively;

The number of capital parameters is preferably greater than 2, 3, 5 and/or less than 50.

Dental Rules

The "dental rules" are rules that impose ranges, defined by the frame of reference, for the values of the dental parameters, that is to say parameters relating to the configuration of the teeth, at the final instant.

The dental rules conventionally used to define conventional orthodontic treatments may be used. They are preferably specific to the patient, and preferably determined by the orthodontist, according to the needs of the patient.

Preferably, a dental rule defines a deviation, possibly equal to zero, from the configuration of the teeth of at least one dental arch of the patient as modeled in a three-dimensional digital model, referred to as the "target model". In other words, it imposes at least one range for a parameter pertaining to a position of a tooth of the patient.

The target model may in particular model the patient's teeth in their desired arrangement at the final instant, that is to say at the end of the complex orthodontic treatment.

The target model may be produced by modifying a three-dimensional digital model of said dental arch, preferably produced less than 3 months before the initial instant, referred to as the "initial model". The initial model is preferably obtained by a scan of said arch.

In general, the capital rules and/or the dental rules are preferably defined less than 6 months, less than 3 months, preferably less than a month, or even less than a week before the initial instant.

Preferably, the regulation is defined, at least partially, on the basis of images acquired at an instant of acquisition. The instant of acquisition precedes step a), preferably by less than 6 months, 3 months, 1 month, preferably by less than a week.

Preferably, at least part of the frame of reference, in particular the limits for the variations in the values of the capital and dental parameters during the complex orthodontic treatment, are defined, at least partially, with images.

Images

Preferably, the images comprise "capital images", showing at least part of the patient's head, and "dental images", showing at least some of the patient's teeth. When a capital image depicts teeth, it is also a dental image.

The images, and in particular the capital images, preferably contain photos, preferably in realistic colors. The photos may be acquired using any camera.

Preferably, at least some of the capital images, preferably all of the capital images, show more than 50%, preferably more than 70%, more than 80%, more than 90%, preferably 100% of the height of the head, from the chin to the top of the skull.

Preferably, the images comprise at least an image of the patient's head seen from the front, an image of the head seen in profile, and a smiling image, preferably a smiling image seen from the front. Preferably, the images also include at least an image of the patient with the mouth open and an image of the patient with the mouth closed.

The images may include photos, x-rays, views of a three-dimensional model obtained from a scan of a dental arch, and/or a combination of such images.

The images, and in particular the dental images, preferably contain x-rays. X-rays are preferably performed by a healthcare professional, for example an orthodontist or an orthodontic laboratory.

The images preferably contain at least one "combined" image, that is to say resulting from a combination of several images. Preferably, at least one combined image represents an overlay of a photo, preferably in realistic colors, with an x-ray, as shown in the example of FIG. 4. The overlay is preferably produced by increasing the transparency of at least one of the images to be overlaid, in particular using a computer program, the images to be overlaid showing the same view, for example a front view or a profile view of the head of the patient.

Preferably, at least some of the images, and in particular of the dental images, are extra-oral images which show the teeth of the patient while the patient is wearing a retractor 20, as in the images of FIG. 3.

Preferably, reference marks are positioned on the images, preferably displayed on the computer screen, preferably by the user, preferably an orthodontist, to define extreme positions identified by noteworthy points. The images thus serve to enter the limits for the variations in these positions.

The reference mark may in particular be a geometric mark, preferably chosen from a point, a straight line, a circle or an arc of a circle.

Preferably, at least one reference mark is chosen from the group consisting of
- at least one pair of points, in particular three pairs of points, for example a first pair comprising a point located in the middle of the forehead on the hairline and
a point between the eyebrow arches, a second pair
comprising a point between the eyebrow arches and a
subnasal point and a third pair comprising a subnasal
point and a pogonion point (a rule defining the vertical
movement of the jaw may be determined on the basis
of one or more of these three pairs of points);
a point located on each of the corners of the patient's lips
when (s)he is smiling, in a front view (a rule defining
the width of the dental arch may be determined on the
basis of these two points);
two points defined by the outermost points of the teeth
closest to the corners of the lips, when these teeth are
oriented parallel to the vertical axis defined by a point
between the eyebrow arches and a subnasal point (a
rule defining a width of maximum or target dentition
may be defined on the basis of these two points);
a straight line passing through a point between the eye-
brow arches and a subnasal point, and an inter-incisal
point of the upper central incisors (a rule defining the
lateral movement of the central incisors may be defined
on the basis of this straight line and this point);
a point located at the junction of the first upper incisors
and a point located at the junction of the first lower
incisors (a rule defining the relative right/left move-
ment of the upper and lower incisors may be defined on
the basis of these points);
a straight line passing through at least two points among
a point between the eyebrow arches, a subnasal point
and/or an inter-incisal point, and a straight line passing
through a point on the cusp of the first left or right
premolar, and a point at the enamel-cementum junction
of the first left or right premolar, respectively (a rule
defining the rotation of the first premolar may be
defined);
an arc of a circle passing for example through two points
located at the corners of the patient's lips seen from the
front and having as its center a point located in the
middle of the lower lip (a rule defining the vertical
movement of at least one of the dental arches may be
defined);
a straight line connecting the tip of the chin to the most
prominent point on the forehead, in an image showing
a side view of the head (a rule delimiting the forward/
backward movement of the chin may then be deter-
mined on the basis of this straight line).
The reference marks may be positioned automatically
using an image analysis method, for example using machine
learning methods, in particular a neural network.
Preferably, instructions are given orally or displayed on a
screen so that the user positions the reference marks manu-
ally, for example using a mouse, a stylus or a finger, by
interaction with a computer touch screen.
Preferably, the computer imposes an order for positioning
the reference marks, which then allows it to establish the
rules accordingly.
In step b), the parameterization blocks of the various basic
orthodontic treatments of the complex orthodontic treatment
are gradually determined and activated, in a predetermined
order. Preferably, step b) is performed by the orthodontist,
preferably in the presence of the patient.
The basic orthodontic treatments are preferably chosen
from the basic orthodontic treatments known from the prior
art for changing the morphology of the head and/or the
configuration of the teeth, in particular for a therapeutic,
prophylactic or esthetic result.

A parameterization block is a key which, when applied to
a basic orthodontic treatment defined by a general function,
for example "change the position of the lower jaw", converts
it into an operational solution, sufficiently defined such that
an orthodontic appliance can be designed to implement this
solution.
According to the invention, the first basic orthodontic
treatment to be parameterized is a capital basic orthodontic
treatment, preferably chosen from among a treatment for
changing the height of the lower jaw, a treatment for
changing the width of the upper jaw, and/or a treatment for
changing the position of the lower jaw in relation to the
upper jaw.
The parameterization block activated must be compatible
with the regulation. For example, if the regulation imposes,
for the final instant, a position of the lower jaw, in the
front-rear direction, of between 0 and 5 mm forward from its
initial position, the complex orthodontic treatment compris-
ing the basic orthodontic treatment parameterized with this
parameterization block must not result in a movement of the
lower jaw which would take it more than 5 mm forward
from its initial position.
Conventionally, there are several parameterization blocks
which are compatible with the regulation. For example, if
the first basic orthodontic treatment is an orthodontic treat-
ment for changing the position of the lower jaw, in the
front-rear direction, there may be several technical solutions
to achieve this change, each of these solutions being the
result of the parameterization of the basic orthodontic treat-
ment with a corresponding parameterization block. To treat
a malocclusion, it is possible to choose a treatment with an
arch wire and brackets or a treatment with orthodontic
aligners, these two treatments being associated with respec-
tive parameterization blocks, to be applied to the basic
orthodontic treatment for "treatment of a malocclusion".
The parameterization blocks possible for a basic orth-
odontic treatment, that is to say the various basic orthodontic
treatments that may be envisaged, as well as the correspond-
ing parameters, are well known to those skilled in the art.
Preferably, the computer determines a group consisting of
parameterization blocks which are compatible with the
regulation, for example by consulting a database established
for this purpose. Preferably, these "potential" parameteriza-
tion blocks are then displayed, preferably on the computer
screen, to the user. Preferably, the group of potential param-
eterization blocks associated with the basic orthodontic
treatment being treated is displayed in the form of one or
more lists, multiple or single choice, displayed on the screen.
The user then chooses one of these potential parameteriza-
tion blocks, that is to say the user activates this block.
In a preferred embodiment, information on the effect of
activating a potential parameterization block is displayed,
preferably in real time, preferably on the computer screen.
For example, the residual margins of variation of values for
one or more parameters of the complex orthodontic treat-
ment are displayed on the computer screen, in particular for
the transverse parameters, preferably for the duration and/or
the cost and/or a pain coefficient and/or a number of ortho-
dontist appointments relating to the active complex orth-
odontic treatment.
Also preferably, the effect of activating the parameteriza-
tion block on one or more "final" values of capital and/or
dental parameters is displayed on the computer screen,
preferably in real time, the final value of a parameter being
the value which would result, at the final instant, from the
complex orthodontic treatment as parameterized at the
instant in question. For example, the computer screen displays the position of the lower jaw expected at the end of the complex orthodontic treatment. In a preferred embodiment, this display is graphical. Preferably, a view of a 3D model of the head and/or teeth, preferably hyperrealistic, showing the final morphology of the head and/or the final configuration of the teeth of the patient is displayed.

Also preferably, the computer allows backtracking within the method. To be specific, the user may return to an earlier parameterization step to do away with the activation of a parameterization block. The user, preferably the orthodontist, may thus test the effect of different potential parameterization blocks before choosing the one to activate definitively.

This real-time control considerably speeds up the parameterization of the complex orthodontic treatment. It also helps train the user, who thus learns to evaluate the effects of activation of the various parameterization blocks. Steps a) and b) of a method according to the invention may thus be used to train an orthodontics student or an orthodontist.

The subsequent basic orthodontic treatments may be capital or dental. They are parameterized following the same procedure as the first basic orthodontic treatment.

Only parameterization blocks which are compatible with the regulation may be selected. To be specific, a parameterization block may only be activated if it is not incompatible with the basic orthodontic treatments previously parameterized. As basic orthodontic treatments are thus parameterized, the number of potential parameterization blocks associated with the basic orthodontic treatments is therefore reduced. The complex orthodontic treatment must always comply with the regulation.

For example, if the maximum cost of the complex orthodontic treatment, imposed by the regulation, is €10,000, and the user chooses, to parameterize the first basic orthodontic treatment, to activate a parameterization block which generates a cost of €2,000, the potential parameterization blocks that will be proposed during the parameterization of the second basic orthodontic treatment, still to be parameterized, cannot generate a cost exceeding €8,000.

As another example, if the second basic orthodontic treatment is an orthodontic treatment for widening the lower jaw, and the first basic orthodontic treatment resulted in the imposition of a position of the lower jaw, in the front-rear direction, of between 0 and 5 mm forward from its initial position, none of the potential parameterization blocks for the second basic orthodontic treatment may result, if activated, in a parameterized complex orthodontic treatment that moves the lower jaw more than 5 mm forward from its initial position, or in a parameterized complex orthodontic treatment that moves the lower jaw backward.

The capital and dental rules limit the variations in the capital and dental parameter values, respectively, during the complex orthodontic treatment, with respect to their initial values.

Verification of compliance of the complex orthodontic treatment with the regulation therefore requires a comparison of the final values of parameters with the frame of reference. The parameterization of the complex orthodontic treatment makes it possible to simulate it and to determine these final values from the initial values of these parameters, that is to say their values at the initial instant.

Preferably, at least some of the initial values are determined with the images, preferably substantially at the same time as the frame of reference is defined, in step a).

The initial values for the capital parameters are preferably determined on the basis of said capital images, that is to say using the information provided by the capital images, for example by measuring a dimension in the capital images.

FIG. 2 shows an example of an image used to determine an initial value for capital parameters relating to the length of the head (distances l1, l2, l3) and relating to the ratio of the height of the upper jaw to the height of the lower jaw (distances l31 and l32).

To determine an initial value from an image, the image is preferably displayed on the computer screen and then the user, preferably an orthodontist, positions one or more measurement marks 10 on the image. Preferably, the computer then calculates an initial value according to the position of the measurement marks, for example the distance between two points positioned by the user. All software known to perform measurements on images may be used.

The measurement mark may in particular be a geometric mark, preferably chosen from a point, a straight line or a circle.

For example, in FIG. 2, the measurement marks 10 are a point between the eyebrows, a subnasal point, a pogonion point, and a point at the upper end of the forehead. The computer may then determine from these points the heights l1, l2 and l3. By adding a point between the lips, the computer may also determine the heights l31 and l32.

FIG. 3 shows an example of determining an initial value for a plurality of parameters relating to the configuration of the patient's teeth shown in three photos. Measurement marks, namely points 101 and straight lines 100 were positioned, automatically or manually, in the images, and measurements of the distance between these measurement marks were performed by the computer to constitute said initial values.

Preferably, at least one measurement mark is chosen from the group consisting of a point between the eyebrows, that is to say halfway between the eyebrows, seen from the front;

a subnasal point, that is to say halfway between the nostrils, under the nostrils, seen from the front;

a pogonion point, that is to say the most prominent point on the end of the chin;

a point at the upper end of the forehead, that is to say located on the hairline, in the middle of the forehead, a point on the cusp point of a tooth;

a point located at the junction between two teeth, in particular at the gum;

a straight line connecting the most prominent point on the forehead and a subnasal point.

A measurement mark, for example a straight line or a circle, may be drawn by the computer from other measurement marks, for example points entered by the user.

Preferably, instructions are given orally or displayed on a screen so that the user positions the measurement marks manually, for example using a mouse, a stylus or a finger, in particular by interaction with a touch screen of the computer.

The measurement marks may be positioned automatically using an image analysis method, for example using machine learning methods, in particular a neural network. Preferably, the measurement marks may be moved by the user, for example using a computer mouse or a stylus or a finger on a tablet. Preferably, the initial values determined from these measurement marks are modified accordingly, preferably in real time.

Preferably, the initial values are displayed on the computer screen, and preferably updated in real time as the user moves measurement marks.

Naturally, the measurement marks may be used to specify, visually and very quickly, several initial values.

The order of parameterization of the basic orthodontic treatments determines a framework for the selection of the parameterization blocks which may vary according to the basic orthodontic treatment in question.

According to the invention, at least one capital basic orthodontic treatment, that is to say relating to the morphology of the patient's head, is parameterized before a dental basic orthodontic treatment, that is to say relating to the configuration of the teeth, is parameterized. Thus, only the parameterization blocks which are not incompatible with this capital basic orthodontic treatment may be activated during the parameterization of the subsequent basic orthodontic treatments.

In one embodiment, several, or even all, of the capital basic orthodontic treatments are parameterized before a dental orthodontic treatment is parameterized.

Preferably, at the end of step b), a report is generated comprising information relating to the regulation, and/or to the initial values and/or to the parameterization blocks activated, and/or to an orthodontic appliance for implementation of the complex orthodontic treatment, and/or to the configuration of the teeth estimated for the final instant and/or to the morphology of the patient's head estimated for the final instant. This report may be displayed to the orthodontist and/or to the patient, for example by being sent or by being displayed, for example on the computer screen. An example of a report is shown in FIG. 5.

The regulation and parameterization of the basic orthodontic treatments may not have resulted in a value being set for each parameter. In other words, the orthodontist may still have, for certain parameters, several options which will each result in a complex orthodontic treatment in accordance with the regulation. In this case, the orthodontist finalizes the parameterization of the complex orthodontic treatment by determining a value for each of the parameters that have not yet been set.

In step c), at least one orthodontic appliance suitable for the complex orthodontic treatment is designed and manufactured. These operations are conventional and pose no problem for an orthodontist.

Preferably, the orthodontic appliance is an orthodontic aligner. The orthodontic appliance may also be a band, an orthodontic wire or any other known orthodontic appliance.

It is then given to the patient, who places it in his/her mouth to undergo the complex orthodontic treatment.

EXAMPLE

At an initial instant, preferably before orthodontic treatment, at least a capital photo of the patient seen from the front, a capital photo of the patient in profile view, a smiling photo seen from the front, a smiling photo in profile view, photos of the patient's teeth seen from the left, the right and the front, and an x-ray of the patient's head seen from the front, are taken. Dental photos are also taken, for example a front view, a left profile view and a right profile view, a dental retractor being worn by the patient during the acquisition of these dental images. These images may also be acquired at different instants in time, preferably the different instants being less than 6 months apart, better still less than two months apart, even better still less than one month apart. Preferably, at least 5 dental and/or capital images, better still at least 10 dental and/or capital images, even better at least 15 dental and/or capital images are acquired.

The images of the patient acquired are then loaded onto a computer.

In step a), the user, preferably the orthodontist, preferably in the presence of the patient, then determines the rules of the regulation. The regulation is determined, at least partially, from said images.

Preferably, the user determines at least one capital rule. FIG. 2 shows an example of determining a capital rule from the reference points in a capital photo of the patient seen from the front. The user may thus, for example, determine a maximum height $13_{max}$ and a minimum height $13_{min}$ by positioning points using a mouse, a stylus or a finger on the computer screen or by entering values with a keyboard. The user also enters measurement points allowing the computer to determine the height of the jaw in the images. In FIG. 2, the height 13, determined using the measurement points 10, in particular a pogonion point and a subnasal point, represents the initial jaw height. A capital rule may be defined by "the final height of the patient's jaw must be within the interval $[13_{min}; 13_{max}]$". A rule may also be defined by entering a maximum variation and a minimum variation with respect to the frame of reference. Thus, another example of a rule, defining a constraint for the height of the patient's jaw may be "the final height of the patient's jaw $13_{finale}$ is between $13+\Delta_{min}$ and $13+\Delta_{max}$", $\Delta_{min}$ and $\Delta_{max}$ corresponding to maximum acceptable for movement of the patient's jaw during the complex orthodontic treatment.

The user then determines at least one dental rule. FIG. 3 shows an example of determining a dental rule on the basis of three dental images of the patient. A dental rule may in particular be determined thanks to the measurement marks $100a; 100b; 101a$ and $101b$. A rule may for example be "a straight line passing through two distinct points located between the upper central incisors and a straight line passing through two distinct points located between the lower central incisors must be substantially coincident at the end of the complex orthodontic treatment" or "a straight line passing through two distinct points located between the upper central incisors and a straight line passing through two distinct points located between the lower central incisors must be substantially parallel and the distance separating these two straight lines must be less than 1 mm at the end of the complex orthodontic treatment". For example, the computer automatically determines measurement lines $100a$ and $100b$ from measurement points $101a$ and $101b$ positioned by the user.

The user then determines at least one transverse rule. Preferably, at least one transverse rule is determined by the patient, and entered into the computer.

A transverse rule may in particular be the determination of a maximum cost of the complex orthodontic treatment, for example "the maximum cost of the complex orthodontic treatment must be less than €10,000", and a maximum duration of the complex orthodontic treatment, for example "the maximum duration of the complex orthodontic treatment must be less than or equal to 1 month".

Preferably, the user also determines a pain and/or comfort coefficient for the complex orthodontic treatment. The pain and/or comfort coefficient is in particular related to the type of orthodontic appliance. The user selects for example a maximum pain threshold acceptable for the patient in relation to a pre-established pain scale, the threshold being for example a number between 0 and 5.

The user may also define rules imposing technical characteristics of the orthodontic appliances to be used for the complex orthodontic treatment, for example "only aligners must be used for the complex orthodontic treatment".

The order in which the rules of the regulation are determined may be changed. In particular, the user may begin by determining all or some of the transverse rules, then all or some of the capital rules, then all or some of the dental rules.

In step b), after having determined at least some of the rules of the regulation, the user prepares the complex orthodontic treatment. To this end, the user selects at least one basic orthodontic treatment, better still several basic orthodontic treatments, from a database of basic orthodontic treatment models and then places them in order. Preferably, a list of potential complex orthodontic treatments each consisting of a predetermined series of basic orthodontic treatments is available and the user chooses a complex orthodontic treatment from this list.

The complex orthodontic treatment preferably includes the following basic orthodontic treatments, classified in the following preferred order of parameterization:

Parametrization of a treatment for moving the lower jaw up/down,

Parametrization of a treatment for widening or narrowing the upper arch and/or the lower arch, Parametrization of a treatment for moving the lower jaw and/or the upper jaw forward/backward;

Parametrization of a treatment for moving the lower jaw left/right;

Parametrization of a treatment for tilting the upper jaw and/or the lower jaw;

Parametrization of a treatment for moving the teeth, preferably a dental occlusion treatment, in particular a supraocculsion, malocclusion or infraocclusion treatment, Parametrization of a treatment for moving the gums and/or moving the upper lip and/or moving the teeth.

Other parametrizations may be added, preferably at the end of the parametrizations as ordered above, for example, a parameterization for changing the color of the teeth. When parameterizing the first basic orthodontic treatment, corresponding potential parameterization blocks that comply with the regulation are displayed to the user, preferably by being displayed on a computer screen. The user then selects a potential parameterization block, thereby activating the selected parameterization block, and/or manually defines a range of acceptable values.

For example, during parametrization of a treatment for moving the lower jaw up/down, the following potential parameterization blocks are displayed: intrusion of the lower molars with a variation included in an interval $[d_{min}; d_{max}]$, intrusion of the lower molars with a variation included in an interval $[d_{min}; d_{max}]$, extrusion of the upper molars with a variation included in an interval $[d_{min}; d_{max}]$, extrusion of the lower molars with a variation included in an interval $[d_{min}; d_{max}]$. The user selects one of these parameterization blocks and enters acceptable values for $d_{min}$ and $d_{max}$.

Alternatively, $d_{min}$ and $d_{max}$ are automatically defined in the potential parameterization blocks "intrusion of the lower molars with a variation included in an interval [0 mm; 5 mm]" or "intrusion of the lower molars with a variation included in an interval [1 mm; 3 mm]", these values being compatible with the regulation. Information relating to the result yielded by the complex orthodontic treatment is preferably displayed on the screen, and updated in real time, in particular after the activation of a parameterization block and/or the selection of a range of acceptable values. The information may relate to the effect of the complex orthodontic treatment on the morphology of the head and/or on the configuration of the teeth, or relate to the cost or the pain associated with the complex orthodontic treatment.

The user may select a potential parameterization block, activate it and thus display the result of this choice. The user may then parameterize the next basic orthodontic treatment or, conversely, modify the parameterization performed if the result is not as desired.

The same procedure is followed for the parameterization(s) of subsequent basic orthodontic treatments, the potential parameterization blocks being dependent on the regulation, but also on the parametrizations of the basic orthodontic treatments performed previously. Thus, the later the parametrization of a basic orthodontic treatment is performed (the further the basic orthodontic treatment is from the first basic orthodontic treatment), the more numerous the constraints that the potential parameterization blocks must respect.

After parameterization of all of the basic orthodontic treatments by the user, a report preferably comprising some of the images of the patient, at least some of the parameterized basic orthodontic treatments, better still all of the parameterized basic orthodontic treatments, at least one representation of the target morphology of the head and/or target configuration of the teeth of the patient, and/or the rules of the regulation, is displayed to the user. The report may in particular make it possible to see the effect of the parameterized complex orthodontic treatment on the head and/or the teeth of the patient, and provide operational indications, intended for the orthodontist, for the execution of the treatment.

There may be several complex orthodontic treatments making it possible to achieve a target morphology of the head and/or a target configuration of the teeth of the patient. The user, preferably the orthodontist, thus finalizes, preferably on the basis of the report, the parameterization of the complex orthodontic treatment. For example, the complex orthodontic treatment may offer two options for the "Nature of orthodontic appliance" parameter for the selection of the orthodontic appliance: "arch wire and brackets"/"aligner". When the parameterization is finalized, a value is set, for example "aligner".

At the end of step b), the definition of an operational orthodontic treatment, adapted to the needs of the patient, is thus achieved.

In step c), an orthodontic appliance suitable for this treatment is designed, preferably automatically, for example by means of a computer, and then manufactured.

Alternatively, the report is displayed only after the orthodontic appliance design step and includes a description of at least some of the parameterized basic orthodontic treatments, and/or a description of the orthodontic appliance to be manufactured.

As is now clear, the invention makes it possible to design an orthodontic appliance adapted to change the configuration of the teeth, like conventional orthodontic appliances, but also to guarantee that this change will not be accompanied by an unacceptable change to the morphology of the head, or indeed, preferably, that it will be accompanied by a change to the morphology of the head desired by the patient and/or the orthodontist.

Naturally, the invention is not limited to the embodiments described above and shown.

In particular, at least part of the frame of reference, in particular the limits for the variations in the values of the capital and dental parameters during the complex orthodontic treatment, may be defined, at least partially, using 3D models, for example acquired by means of a scanner. These 3D models preferably contain a dental model showing at least some of the patient's teeth and/or a capital model showing more than 50%, preferably more than 70%, more than 80%, more than 90%, preferably 100% of the patient's head.

In particular, the patient is not limited to a human being. A method according to the invention may be used for another animal.

The invention claimed is:

1. A method for manufacturing at least one orthodontic appliance intended to be worn by a patient, for the implementation, from an initial instant to a final instant, of a complex orthodontic treatment consisting of at least one first basic orthodontic treatment configured to change the morphology of the patient's head and at least one second basic orthodontic treatment configured to change the configuration of the patient's teeth, said method comprising the following steps:

a) determination, using a computer, of a regulation defining rules for the complex orthodontic treatment; then b) parameterization, using a computer, of said at least one first basic orthodontic treatment, then of said at least one second basic orthodontic treatment, in such a way that after said parameterization, the complex orthodontic treatment still complies with said rules;

c) design, using a computer, and manufacture of at least one orthodontic appliance adapted to said complex orthodontic treatment, wherein the regulation defines;

at least one capital rule relating to the morphology of the patient's head, at least one dental rule relating to the configuration of the patient's teeth, and at least one transverse rule which is neither a capital rule nor a dental rule, said at least one capital rule concerning a value chosen from the group consisting of a height of the patient's face at the final instant, and a position of the patient's lower lip and/or the patient's upper lip in relation to the patient's chin and to the patient's forehead;

said at least one transverse rule concerning a value chosen from the group consisting of a cost for the complex orthodontic treatment, a duration for the complex orthodontic treatment, a pain coefficient for the complex orthodontic treatment, a comfort coefficient for the complex orthodontic treatment, one or more technical characteristics for said at least one orthodontic appliance.

2. The method as claimed in claim 1, wherein the complex orthodontic treatment comprises a basic orthodontic treatment chosen from the group consisting of:

a treatment for moving the lower jaw up or down;

a treatment for changing the width of the upper jaw;

a treatment for changing the width of the lower jaw;

a treatment for moving the lower jaw forward or backward;

a treatment for moving the upper jaw forward or backward;

a treatment for moving the lower jaw laterally;

a treatment for changing the transverse tilt of the jaws;

a treatment for moving one or more teeth;

a treatment for moving the gums;

a treatment for changing the color of one or more teeth.

3. The method as claimed in claim 1, wherein the basic orthodontic treatments are placed in order so as to be parameterized in the following order of parameterization:

parameterization of a treatment for moving the lower jaw;

parametrization of a treatment for changing the width of the upper jaw;

parametrization of a treatment for changing the width of the lower jaw;

parametrization of a treatment for moving the lower jaw forward/backward;

parametrization of a treatment for moving the upper jaw forward/backward;

parametrization of a treatment for moving the lower jaw to the right/left;

parametrization of a treatment for tilting the jaws;

parametrization of a treatment for moving one or more teeth;

parametrization of a treatment for moving the gums;

parametrization of a treatment for changing the color of one or more teeth.

4. The method as claimed in claim 1, wherein the regulation defines:

at least one capital rule relating to the morphology of the head, concerning a value chosen from the group consisting of a height of the lower jaw and/or a height of the upper jaw at the final instant;

a width of the lower jaw at the final instant, a position of the lower jaw in relation to the upper jaw, at the final instant, a width of the upper jaw at the final instant;

at least one dental rule relating to the configuration of the teeth, concerning a value chosen from the group consisting of:

a distance with respect to a target configuration of the teeth at the final instant;

a tilt with respect to a target configuration of the teeth at the final instant;

a movement of the gums with respect to a target configuration of the teeth at the final instant;

a target color of the teeth at the final instant.

5. The method as claimed in claim 1, wherein to check, at an instant in step b), whether the complex orthodontic treatment complies with said rules, dimensions, in images and/or 3D models displayed on a computer screen, are measured between noteworthy points in said images and/or in said 3D models, said dimensions constituting initial values of parameters of the complex orthodontic treatment, the effect of the complex orthodontic treatment, as parameterized at said instant in step b), is simulated on said dimensions, between the initial instant and the final instant, so as to determine final values for said parameters, then it is checked whether said final values fall within corresponding ranges defined by the rules of the regulation.

6. The method as claimed in claim 5, wherein, to determine said initial values noteworthy points are identified in the images and/or the 3D models, and measurement marks are arranged as a function of the noteworthy points, said computer determining said initial values as a function of the arrangement of said measurement marks, or the images and/or the 3D models are analyzed by computer using a machine learning method to determine said initial values.

7. The method as claimed in claim 5, wherein, to define at least one limit of a said range relating to a position of a noteworthy point of the patient, at least one reference mark is arranged in at least one of said images and/or one of said 3D models, the position of the reference mark indicating an extreme position for said noteworthy point at the final instant, and thus defining said limit.

8. The method as claimed in claim 5, wherein said images comprise at least:

an image from the front and a profile image of the head of the patient, and/or an image showing the patient's mouth in the open position and at least one image showing the patient's mouth in the closed position, and/or an image showing the patient's mouth in the smiling position, and/or a panoramic image, and/or an x-ray of the head of the patient;

and/or said 3D models comprise at least a 3D model of the face, and/or a 3D model of the inside of the mouth, referred to as intraoral, in particular a 3D model of the teeth and/or a tomographic image or cone beam scan.

9. The method as claimed in claim 1, wherein the regulation may be modified at any instant during the parameterization of the basic orthodontic treatments, as long as the complex orthodontic treatment, as parameterized up to this instant, complies with the regulation.

10. The method as claimed in claim 1, wherein to parameterize a basic orthodontic treatment, a parameterization block is chosen from a group of potential parameterization blocks potentially applicable to the basic orthodontic treatment so as to parameterize same, the computer then parameterizing the basic orthodontic treatment with said parameterization block, said group of potential parameterization blocks comprising only parameterization blocks which, when applied to the basic orthodontic treatment, result in a complex orthodontic treatment that complies with the regulation.

11. The method as claimed in claim 1, wherein at an instant during the parameterization, information is displayed on a computer screen and is updated in real time, this information relating to the regulation, and/or parameters of the complex orthodontic treatment, and/or the morphology resulting, at the final instant, from the complex orthodontic treatment as parameterized at said instant, and/or the final configuration of the teeth resulting, at the final instant, from the complex orthodontic treatment as parameterized at said instant.

12. The method as claimed in claim 1, wherein, in step c), an orthodontic aligner is manufactured.

13. The method as claimed in claim 1, wherein after in step c), a report is generated comprising information relating to the regulation, and/or complex orthodontic treatment parameters, and/or the morphology resulting from the complex orthodontic treatment at the final instant, and/or the final configuration of the teeth resulting from the complex orthodontic treatment at the final instant.

14. The method as claimed in claim 1, wherein said parameterization is displayed to a user to train said user in orthodontics.

15. The method as claimed in claim 1, wherein any first basic orthodontic treatment is parameterized before any second basic orthodontic treatment.

16. A kit comprising:

a device for acquiring images and/or 3D models;

a non-transitory computer-readable medium encoded with a computer program comprising code instructions for the execution of steps a), b), and c) of the method of claim 1 when said computer program is executed by a computer.

* * * * *